US006179795B1

(12) United States Patent
Garza

(10) Patent No.: US 6,179,795 B1
(45) Date of Patent: Jan. 30, 2001

(54) ADULT NOVELTY DEVICE

(76) Inventor: Ronaldo Arturo Garza, 5704 E. Aire Libre, #1231, Scottsdale, AZ (US) 85254

( * ) Notice: Under 35 U.S.C. 154(b), the term of this patent shall be extended for 0 days.

(21) Appl. No.: 09/299,244

(22) Filed: Apr. 26, 1999

(51) Int. Cl.[7] ................................ A61H 7/00; A61F 5/00
(52) U.S. Cl. ................................ 601/97; 600/38
(58) Field of Search ................................ 601/97, 89, 84, 601/134, 135, 136, 137; 600/38, 39

(56) References Cited

U.S. PATENT DOCUMENTS

| | | | | |
|---|---|---|---|---|
| 4,722,327 | * | 2/1988 | Harvey | 601/97 |
| 4,790,296 | * | 12/1988 | Segal | 601/97 |
| 5,470,303 | * | 11/1995 | Leonard et al. | 601/84 |
| 5,472,399 | * | 12/1995 | Szekely | 600/38 |
| 5,690,604 | * | 11/1997 | Barnett | 600/38 |
| 5,725,473 | * | 3/1998 | Taylor | 600/38 |
| 5,851,175 | * | 12/1998 | Nickell | 600/38 |

* cited by examiner

*Primary Examiner*—Michael A. Brown
*Assistant Examiner*—Benjamin K. Koo

(57) ABSTRACT

An adult novelty device for simulating sexual encounters by a user lying in a reclined position. The device includes a pivot base aligned along an axis perpendicular to the length of the user and generally within the plane of the reclined position. A leg portion, joined to the pivot base by a knee joint, extends upward to permit the leg portion to move in an arc closer to and away from the user. A sleeve assembly is mounted on the leg portion and is aligned for sexual engagement with the user in at least one body orifice by a sleeve mounted on the other end of the assembly. The user is able to move the sleeve by a driver assembly attached to the leg, whereby the user can move the leg portion toward and away from the user's body orifice by pivoting the leg portion about the knee joint to cause movement of the sleeve assembly. In a preferred embodiment, the pivot base includes a pair of pivot base blocks holding down a base rod on both ends of the base rod, whereby the knee joint pivots on the rod to permit rotation of the knee joint about the rod. Also preferred is to adjustably mount the sleeve assembly and/or the driver assembly on the leg to permit adjustment of the angle with respect to the horizontal position of the user.

12 Claims, 2 Drawing Sheets

ADULT NOVELTY DEVICE

BACKGROUND OF THE INVENTION

Various devices have been proposed as adult novelty devices, having varying degrees of realism and complication. For example, devices have been proposed which function as a female functional mannequin for use by adult males. These devices are said to be useful as a simulation of a female in a functionally operative mannequin for use by a male to deposit sperm, whether for medical or personal purposes. Such mannequins can be used within sperm banks and also by psychiatrists in treating people with sexual disorders. Other uses are to decrease the transmission of AIDS and other sexually transmitted diseases and also, perhaps, to decrease prostitution and, possibly, even rape and molestation. It is also noted that such mannequins could be used by people incarcerated within jails, by persons with certain disabilities or, for whatever reason, do not have access to a human female partner.

Other attempts to provide devices which serve as a substitute for or as an aid with a partner have been developed. Most of these devices are quite complicated, particularly those which are mechanically driven or operated during use. For example, Segal U.S. Pat No. 4,790,296 discloses an adult sex device using a cam-driven drive shaft for translating rotating motion into reciprocating and linear motion using an electric motor. The device is mounted on a stand. Also, Fuhrman et al U.S. Pat. No. 5,385,154 discloses a complicated chair assembly in which a couple cooperatively act with a reduced effect of gravity. Mitchum U.S. Pat. No. 5,453,080 has a similar device.

Boutos U.S. Pat. No. 5,586,560, Boutos U.S. Pat. No. 5,704,894, and Boutos U.S. Pat. No. 5,857,690, all being related patents, comprise seating devices using pneumatically driven components for adult sexual use. Taylor U.S. Pat. No. 5,725,473 is also motor driven and is designed to appear like a male engaged in sexual intercourse with the user.

All of the devices above are very complicated, require delicate balance or alignment, or are so large as to take up quite a bit of room. While in some cases the space occupied by an adult novelty device may be of no concern, matters of privacy and discretion often times require the device to be out of sight when not in use. Large devices like shown in the prior art require either disassembly or a special private area in the home or other location.

Similarly, very small, hand held devices afford adequate privacy and simplified storage, but do not provide the appropriate opportunity for full engagement by the user. However otherwise appealing, hand held devices remain simply that—hand held—and do not convey the concept of partnership sexual relationships.

Accordingly, it is an object of the present invention to provide a device which is simple to construct and easily stored while still giving the user a sense of having relations with another.

Another object of this invention is to provide a device that is adjustable to permit different positions and match the specific size needs of users of different physical dimensions.

Other objects will appear hereinafter.

SUMMARY OF THE INVENTION

It has now been discovered that the above and other objects of the present invention may be accomplished in the following manner. Specifically, the present invention provides a hand driven device (although it does not need to be so limited) which pivots about a horizontal base bar at the knee junction and is driven by a driver assembly to move a sleeve assembly for the purpose intended. The pivot coupler assemblies permit personalized adjustment of the device to suit individual users.

In its simplest form, the present invention comprises a leg portion, joined to a pivot base by a knee joint, extending upward to a predetermined height, depending on the user's size, to permit the leg portion to move in an arc closer to and away from the user. A sleeve is mounted on the leg portion in alignment for sexual engagement with the user in at least one body orifice. The user can move the sleeve by moving the leg portion toward and away from the user's body orifice using a driver arm to pivot the leg portion about the knee joint to cause movement of the sleeve in engagement with the body orifice.

In one embodiment, the pivot base includes a pair of pivot base blocks supporting a base rod on both ends of the base rod, whereby the knee joint pivots on the rod to permit rotation of the knee joint about the rod.

In another embodiment, the sleeve assembly and/or the driver assembly is adjustably mount on the leg to permit adjustment of the angle with respect to the horizontal position of the user.

Also preferred is to use an adjustable coupling device for mounting and positioning the sleeve assembly and driver assembly for personalization of the device for the specific user.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
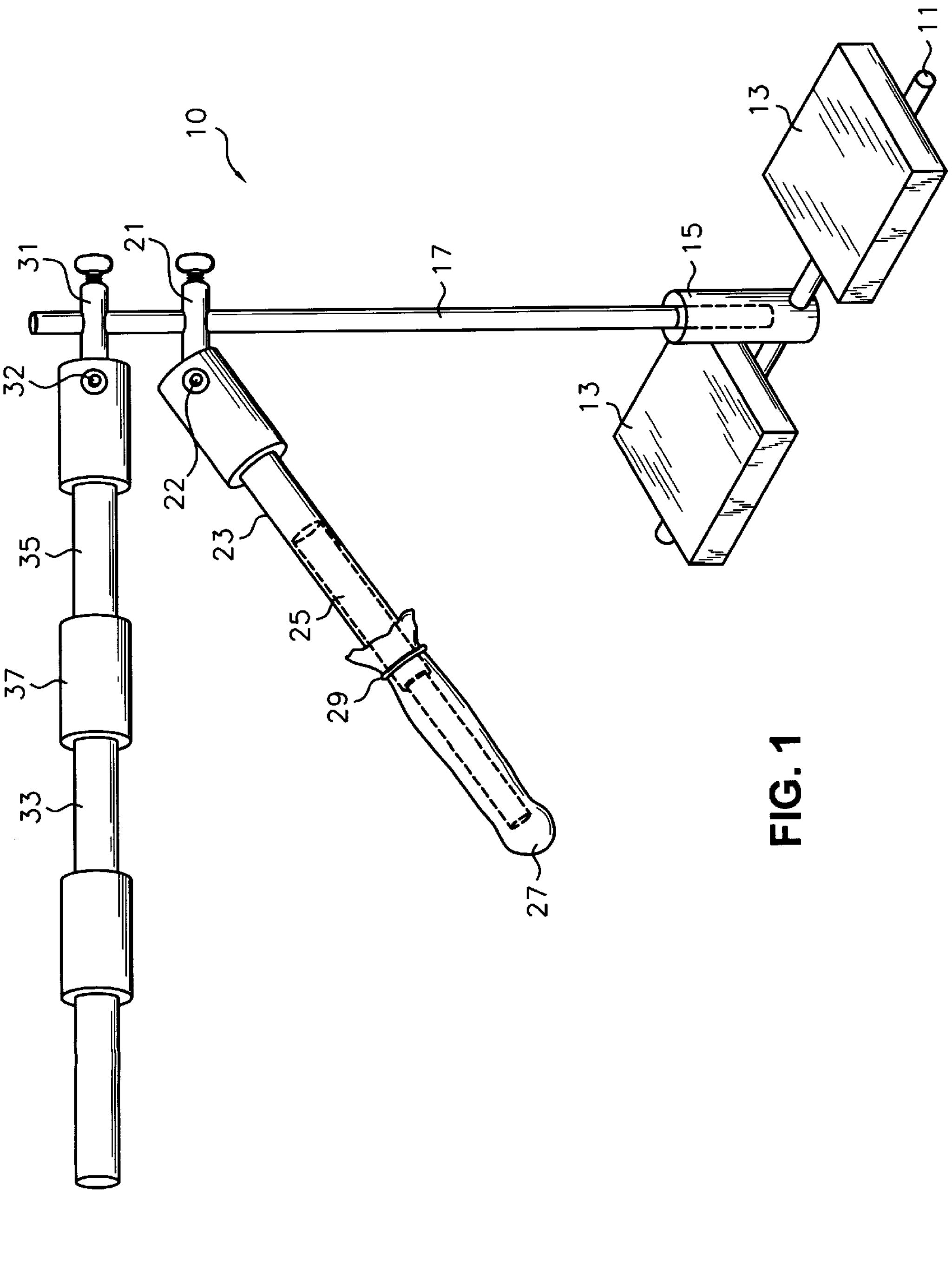
FIG. 1 is a perspective view, schematically showing the device of the present invention.

As shown in the drawings, a device 10, generally, includes a pivot base 11, usually in the form of a rod made from metal or plastic, which may be used alone or fitted into base weights 13 as shown in FIG. 1. Pivot base 11 passes through knee joint 15 which mounts a leg portion 17. Leg portion 17 may be round or square, with the latter being preferred, and may be made from metal, plastic and other materials.

Mounted near the top of leg portion 17 is a first fastener 21, having an adjustable pivot 22, for positioning sleeve assembly 23. Inside sleeve assembly 23 is an optional stiffener 25, which is to be used if sleeve assembly 23 is fabricated from plastic or other reasonably flexible materials. Sleeve assembly 23 terminates in a sleeve 27, shown mounted via "o" ring 29 in FIG. 1. Sleeve 27 is designed for engagement with an orifice of the user, and may be a simple cylindrical sleeve or, optionally, have the shape of the male sex organ or other shapes as desired. Pivot 22 allows the user to adjust the angle and height of sleeve assembly 23 for most comfortable and pleasing use.

Mounted above first fastener 21 on leg portion 17 is a second fastener 31, with pivot 32, which mounts a driver assembly 33. Driver assembly 33 is shown in FIG. 1 as comprising several rods 35 connected together via connectors 37 to provide a suitable length for the user to reach. As can be appreciated, the driver assembly is moved by the user (or a companion, if desired) so as to pivot leg portion 17 about pivot base 11 via knee joint 15, which movement causes sleeve assembly 23 and thus sleeve 27 to move toward and away from the user. By suitable alignment, the movement can bring sleeve 27 into contact with and entry into a body orifice, such as the female sex organs.

Use of the device is intended for personal pleasure and suitable lubricants and proper selection of manufacturing materials are intended to be part of the invention. There are many suitable sleeves available in the adult novelty market, and any such sleeves may be used, depending on the desires of the user.

Figure 2:
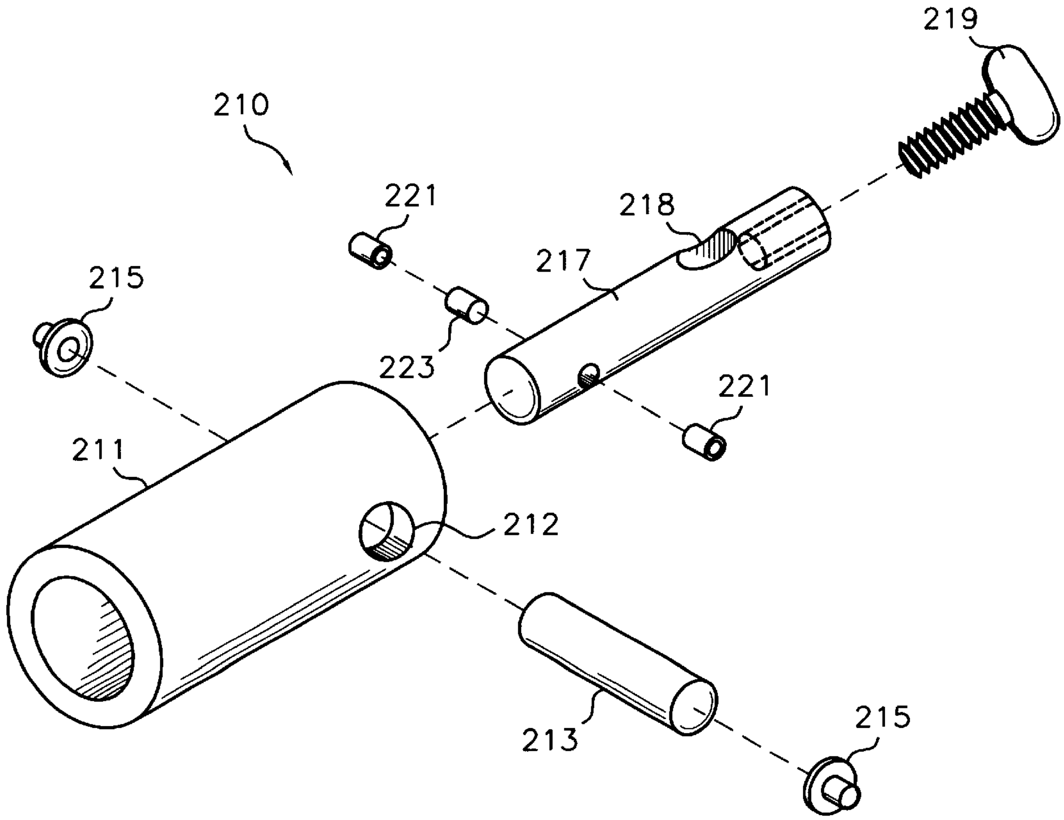
FIG. 2 is an exploded view of one embodiment of a portion of the invention.

FIG. 2 illustrates one form of fastener, 210 generally, such as fasteners 21 and 31 in FIG. 1. This fastener has a body 211 for engagement with the sleeve assembly or driver assembly shown above, with hole 212 through which pivoting rod 213 passes into body 211, and is fastened via axle hat nuts 215. Pivoting rod 213 also passed through a pivot block 217, spaced from the inside walls of body 211 by spacers 221 and, if pivot block 217 is not plastic, a silencing tube 223. This fastener is mounted on to leg portion 17 to support either or both sleeve assembly 23 and/or driver assembly 33 by thumb screw 219 being tightened against leg portion 17 which has been passed through hole 218 and put in the desired position as previously described.

Figure 3:
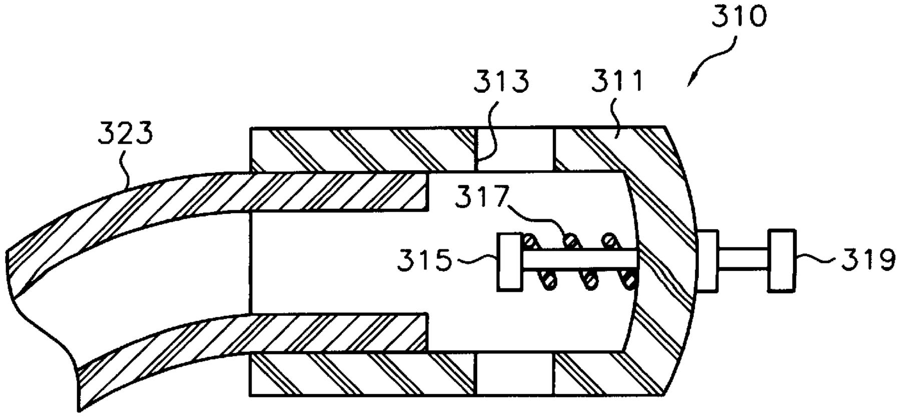
FIG. 3 is a schematic, side elevational view in section of a second, preferred embodiment of the portion of the invention shown in FIG. 2.

FIG. 3 illustrates a more preferred fastener, 310 generally, which is simpler and easier to manufacture and use. Body 311 includes a hole 313 through which leg portion 17 passes. Fastener base 315 engages leg portion 17 and is maintained there against by spring 317. Pulling on end 319 compresses spring 317 and allows for the previously discussed adjustment and placement of sleeve assembly 23 and/or driver assembly 33. Body 311 may also be attached to either sleeve assembly 23 and/or driver assembly 33 by a semi-flexible extension 323, rather than the pivot previously described. As long as extension 323 is adjustable but capable of remaining generally where it is positioned by the user during use unless intentionally moved, this embodiment allows for some additional flexibility to more nearly simulate natural acts.

As can be appreciated, the device of this invention is intended for use by a user lying in a reclined position, reaching up to grasp and move driver assembly 33 with one or both hands to cause sleeve assembly 23 to move toward and away from the user by pivoting of leg portion 17 about pivot base 11 via knee joint 15. Sleeve 27 engages the user as desired.

While particular embodiments of the present invention have been illustrated and described, it is not intended to limit the invention, except as defined by the following claims.

What is claimed is:

1. An adult novelty device for simulating sexual encounters by a user lying in a reclined position, comprising:

a pivot base aligned along an axis perpendicular to the length of said user and generally within the plane of said reclined position;

a leg portion extending upward from said plane for a predetermined distance, said leg portion being joined to said pivot base by a knee joint, said knee joint permitting said leg portion to move in an arc closer to and away from said user;

a sleeve assembly mounted at one end on said leg portion and extending toward said user and aligned for sexual engagement with said user in at least one body orifice, said sleeve assembly having a sleeve mounted on the other end for physical engagement with said user; and a driver assembly mounted on said leg portion and extending toward said user to a position within reach of said user, whereby said user can move said leg portion toward and away from engagement with said user's body orifice by pivoting said leg portion about said knee joint to cause movement of said sleeve assembly and engagement of said sleeve with said user.

2. The device of claim 1, wherein said pivot base includes a pair of pivot base blocks holding down a base rod and positioned on both ends of said base rod, whereby said knee joint is pivotally mounted on said base rod between said pivot base blocks to permit rotation of said knee joint about said rod.

3. The device of claim 2, wherein said sleeve assembly is adjustably mounted on said leg portion to permit adjustment of the angle said sleeve makes with respect to the horizontal position of said user.

4. The device of claim 1, wherein said driver assembly is adjustable along the length thereof permit adjustment of said position within reach of said user.

5. The device of claim 1, wherein said sleeve assembly is attached to said leg portion by a pivoted coupler.

6. The device of claim 5, wherein said driver assembly is attached to said leg portion by a pivoted coupler.

7. An adult novelty device for simulating sexual encounters by a user lying in a reclined position, comprising:

pivot base means aligned along an axis perpendicular to the length of said user for supporting said device, said pivot base means being generally within the plane of said reclined position;

leg portion means for extending upward from said plane for a predetermined distance, said leg portion means being joined to said pivot base by knee joint means for moving said leg portion in an arc closer to and away from said user;

sleeve assembly means mounted at one end on said leg portion for extending a sleeve toward said user, said sleeve assembly means being aligned for sexual engagement between a sleeve there on and said user in at least one body orifice, said sleeve assembly means mounting said sleeve on the other end for said sexual engagement with said user; and driver assembly means for driving said device, said driver assembly means being mounted on said leg portion means and extending toward said user to a position within reach of said user, whereby said user can move said leg portion means toward and away from engagement with said user's body orifice by pivoting said leg portion means about said knee joint means to cause movement of said sleeve assembly means and engagement of said sleeve with said user.

8. The device of claim 7, wherein said pivot base means includes pivot base block means holding down a base rod and positioned on both ends of said base rod, whereby said knee joint means is pivotally mounted on said base rod between pivot base block means to permit rotation of said knee joint means about said rod.

9. The device of claim 8, wherein said sleeve assembly means is adjustably mounted on said leg portion means to permit adjustment of the angle said sleeve makes with respect to the horizontal position of said user.

10. The device of claim 7, wherein said driver assembly means is adjustable along the length thereof to permit adjustment of said position within reach of said user.

11. The device of claim 7, wherein said sleeve assembly means is attached to said leg portion means by pivoted coupler means for attaching said leg portion means.

12. The device of claim 11, wherein said driver assembly means is attached to said leg portion means by pivoted coupler means for attaching said leg portion means.

* * * * *